(12) United States Patent
Jin et al.

(10) Patent No.: US 8,197,694 B1
(45) Date of Patent: Jun. 12, 2012

(54) SAFE TRANSPORTATION AND STORAGE FOR CAPILLARY COLUMNS

(76) Inventors: Chaodong Jin, Harrison, NJ (US);
Qiangwei Xia, Madison, WI (US)

( * ) Notice: Subject to any disclaimer, the term of this patent is extended or adjusted under 35 U.S.C. 154(b) by 331 days.

(21) Appl. No.: 12/750,152

(22) Filed: Mar. 30, 2010

(51) Int. Cl.
*B01D 15/08* (2006.01)

(52) U.S. Cl. .................................. 210/656; 210/198.2

(58) Field of Classification Search .................. 210/635, 210/656, 198.2; 73/61.52; 95/82; 96/101; 402/52, 65
See application file for complete search history.

(56) References Cited

U.S. PATENT DOCUMENTS

| | | | |
|---|---|---|---|
| 4,636,316 A * | 1/1987 | Harris et al. .................. | 210/656 |
| 4,966,695 A * | 10/1990 | Joshua ........................ | 210/198.2 |
| 5,165,813 A | 11/1992 | Kageyama et al. | |
| 5,549,404 A | 8/1996 | Kageyama et al. | |
| 5,662,425 A | 9/1997 | Mitsuya | |
| 5,788,118 A | 8/1998 | Kageyama et al. | |
| 5,803,637 A | 9/1998 | Mitsuya | |
| 5,938,919 A | 8/1999 | Najafabadi | |
| 5,961,236 A | 10/1999 | Kageyama | |
| 7,575,676 B2 * | 8/2009 | Prentice et al. ............. | 210/198.2 |
| 2005/0011835 A1 * | 1/2005 | Henderson et al. ........... | 210/656 |
| 2006/0060515 A1 * | 3/2006 | Benevides et al. ......... | 210/198.2 |
| 2009/0230045 A1 * | 9/2009 | Kaneko et al. ............. | 210/198.2 |

OTHER PUBLICATIONS

Pentel Co. Ltd. of Japan: Sharp Kerry brand mechanical pencil; http://www.pentel.com/catalog_product.php?id=690.

* cited by examiner

*Primary Examiner* — Ernest G Therkorn
(74) *Attorney, Agent, or Firm* — David Pressman

(57) ABSTRACT

A holder for capillary columns (130) is realized by a mechanical holding device, also called a lead holder, which can be a mechanical pencil. The user holds the holding device in one hand and presses on an actuator (100) at the top of the holder, springably urging a plurality of jaws (115) to open. The user then slidably inserts the capillary column into the holder a desired distance and releases the actuator, causing the jaws to close around the capillary column and hold it in position within the holder. Next, a cap (140, 140') is optionally slidably urged over the end of the holder in order to protect the exposed tip (135) of the capillary column. Removal of the capillary column is accomplished by reversing the above procedure to release the capillary column, allowing the column to be withdrawn.

20 Claims, 1 Drawing Sheet

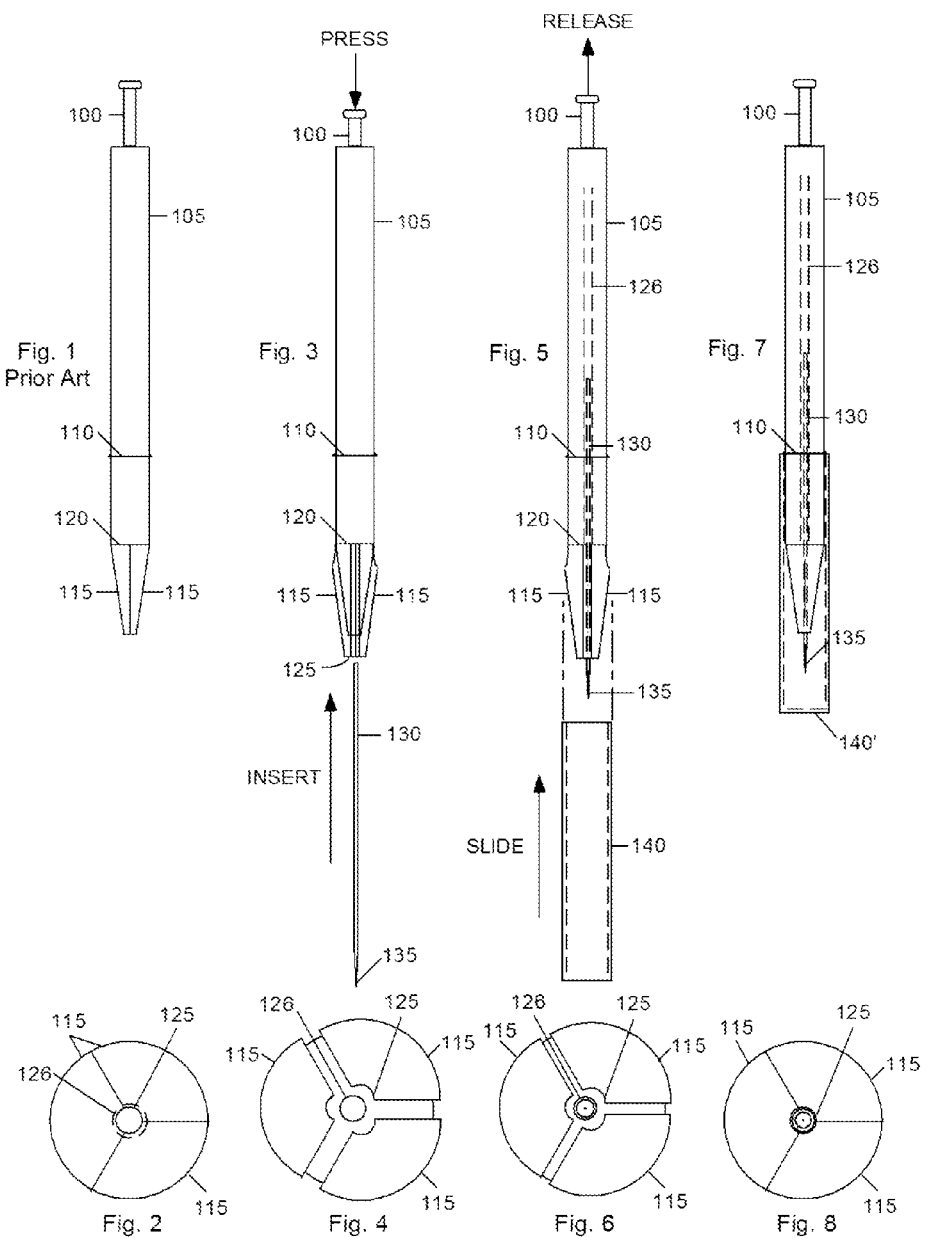

SAFE TRANSPORTATION AND STORAGE FOR CAPILLARY COLUMNS

BACKGROUND

1. Field

The field is packaging and in particular packaging for transporting and storing capillary columns.

2. Prior Art

Capillary columns or tubes, especially ones with integrated emitter or spray tips, are commonly used in the field of analytical chemistry for the chromatographic separation of mixtures that differ in their physical and chemical properties. In the field of liquid chromatography coupled with electrospray ionization mass spectrometry (ESI-MS), analytes are first loaded onto a capillary column, then separated by eluting them off the column at different time points, and subsequently sprayed through the tip into the mass spectrometer where they are analyzed. Typically these columns are installed on the liquid chromatography system with the tip end pointing towards the ion source of the mass spectrometer, within a distance of a few millimeters.

The integrity of the tip ends of the capillary columns greatly affects the ESI efficiency; thus the columns must be shipped, stored, and handled with great care. Typical capillary columns are very fine and not especially fragile, although their tips are very fragile. A capillary column is tubular, typically 360 μm (14 mils) in outer diameter, 50-100 μm (1.9-3.9 mils) in inner diameter, and 10-20 cm (3.9-7.8 in) in length, although other lengths and diameters are used. The tip is formed by tapering one end of the column or tube. A typical tip is shown in FIG. 3 at 135 and is typically 2 to 5 mm long and has inner and outer diameters varying between 1 and 10 μm (0.039-0.39 mils).

Prior art packaging and shipping containers for capillary columns usually comprised densely packed, specialized boxes such as those sold by New Objective, Inc., of Woburn, Mass. A user (researcher or lab technician) removed each column from the box with a rubber-tipped forceps. This required great care due to the high fragility of the tip, as illustrated by the New Objective website, which has the following instructions: "Avoid bending emitter (spray tip) towards you. Although polyimide-coated fused-silica is pliable, should you lose contact with the emitter it may snap back, causing damage to the tip." Moreover, it is not practical to put the columns back into the box. Thus the boxes are used by the manufacturer for transporting the columns to the end user but generally are not used in the laboratory for storing columns.

In the laboratory, after removal from their shipping container and before use, the columns are often taped to workbench shelves or the outside of the shipping box. Alternatively, they are sometimes stored in test tubes with their tips extending upward from the test tube, exposing them to potential damage, as well as airborne dust, which can cause deteriorated ESI performance.

Insofar as we are aware, there is no satisfactory way of holding or storing and dispensing individual capillary columns safely, without the need for forceps, while protecting the columns, and especially their tips, from damage.

SUMMARY

To protectively hold and dispense fine capillary columns, a mechanical pencil or thin rod-holding and dispensing body is employed. It comprises a tube or holding body with a springably opened chuck that holds the column and provides an improved container for storing and dispensing the columns. With the chuck open a column is partially inserted into the holding body for storage with the spray tip of the column extending outward. The chuck is closed to grasp and retain the column. A cap, not normally present on chuck-type pencil lead holders, is assembled to the body to protect the tip of the column. The column is dispensed for use by pressing an operating button to open the chuck and release the column so that it can be retrieved by manual extraction or can fall out by gravity.

BRIEF DESCRIPTION OF THE DRAWINGS

FIGS. 1 and 2 show side and end views, respectively, of a prior-art mechanical pencil according to one aspect of one embodiment.

FIGS. 3 and 4 show side and end views of the pencil of FIG. 1 in an open condition being used as a holder and ready to receive a capillary column.

FIGS. 5 and 6 show side and end views of the pencil or holder of FIG. 1 with a capillary column inserted into the holder and an open-ended protective cap ready to slide on the holder.

FIGS. 7 and 8 show side and end views of the holder of FIG. 1 with the capillary column securely held within and a closed-end cap secured to the end of the holder.

| DRAWING FIGURE REFERENCE NUMERALS | | | |
|---|---|---|---|
| 100 | Actuator | 105 | Body |
| 110 | Stop | 115 | Jaws |
| 120 | End | 125 | Lumen |
| 126 | Lumen | 130 | Capillary |
| 135 | Tip | 140 | Cap |

PREFERRED EMBODIMENT—DESCRIPTION AND OPERATION—FIGS. 1 THROUGH 8

According to one aspect of a preferred embodiment, we use a known mechanical pencil or similar elongated rod holding device to hold and dispense capillary columns safely and conveniently.

FIGS. 1 and 2 show side and end views, respectively of a prior-art mechanical pencil or lead holder that we use to hold and dispense capillary columns. A variety of such mechanical pencils or lead holders, is made in various sizes by various manufacturers. One suitable brand is made by Koh-I-Noor Hardtmuth in the Czech Republic.

The following is a list of some patents and NPL (non-patent literature) that show holders of elongated rods or items to provide additional background; the disclosures of these references are incorporated by reference:

| Pat. or Pub. No. | Kind Code | Issue or Pub. Date | Patentee or Applicant |
|---|---|---|---|
| 5,165,813 | B1 | Nov. 24, 1992 | Kageyama et al. |
| 5,549,404 | B1 | Aug. 27, 1996 | Kageyama et al. |
| 5,662,425 | B1 | Sep. 02, 1997 | Mitsuya |
| 5,788,118 | B1 | Aug. 04, 1998 | Kageyama et al. |
| 5,803,637 | B1 | Sep. 08, 1998 | Mitsuya |
| 5,938,919 | B1 | Aug. 17, 1999 | Najafabadi |
| 5,961,236 | B1 | Oct. 05, 1999 | Kageyama |

Sharp Kerry mechanical pencil of Pentel Co., Ltd. of Japan, shown at http://www.pentel.com/catalog_product.php?id=690.

The Sharp Kerry pencil has "dual-purpose cap" that "provides proper balance while writing and protects [the] writing point when [the] pencil is not in use."

In their '813 patent, Kageyama et al. show a container with a snap-in chuck and chuck ring for holding and dispensing a stick-shaped material such as an eraser.

In their '404 patent, Kageyama et al. show a sealed container and supply cassette for a stick-shaped item in which the stick is held in an cylinder with external helical grooves that are engaged with a non-rotating portion in the body of an outer cylinder comprising the container. The stick is dispensed as the grooves are urged to turn against the non-rotating portion. A cap detachably fits the inner cylinder or the outer cylinder or both.

In his '425 and '637 patents, Mitsuya shows a stick-shaped item-propelling container comprising a guide sleeve and a tubular body. The item is extended from or retracted into the container by rotating the guide sleeve relative to the body.

In their '118 patent, Kageyama et al. show a pencil lead dispensing storage container that can be operated by a single hand. A gate at one end of the container springably opens to permit leads to leave the body of the container, one at a time.

In his '919 patent, Najafabadi shows a flexible tube surrounding the full length of a fused silica capillary liquid chromatography column. The flexible tube is assembled onto the fused silica capillary before packing the column with packing material to protect the capillary during the packing process and is integrated into the finished product.

In his '236 patent, Kageyama shows a dispenser for selectively extending and retracting a stick-shaped object. The dispenser has an additional chamber for storing at least one spare stick-shaped object.

Returning to FIG. 1, the pencil or holder comprises a movable actuator or pushbutton 100, a body 105, a stop 110, and a plurality of springably openable sector jaws 115 which extend from and are contiguous with the lower end 120 of body 105. As shown in FIG. 4, each jaw comprises a sector-shaped member having a large circular segment outside surface, two flat inside surfaces, and a small circular segment inside surface that partially defines the lumen of the jaws. In lieu of sector jaws, any other actuable gripping means can be used.

An internal spring (not shown) urges actuator 100 and jaws 115 upward within body 105 when the holder is in a normal or relaxed state. This holder was designed to hold and dispense leads or graphite rods having a diameter of 0.7 mm (27.56 mils) and 5.1 cm (2 in) long. Thus it is suited to hold and dispense capillary columns having an outer diameter of 0.7 mm. However a similar holder can be specially manufactured or purchased to accommodate this size, or any other size, of capillary column. Other brands of holders can be used if they are designed to hold and dispense leads with the same or a similar diameter as the size of capillary column to be held.

In lieu of the jaws shown, any other type of rod gripping means can be employed, such as a friction holder, a springy holding column, screw-based (the lead is advanced by twisting a screw, which moves a slider down the barrel of the pencil), twist-based (the lead advances upon twisting the head of the pencil).

In FIGS. 1 and 2 where the holder is in a relaxed state, jaws 115 rest in contact with each other in their closed positions. Although three jaws are shown, holders are available with four jaws. Two jaws would also be workable. Jaws 115 are springably loaded to the closed position shown in FIG. 1 but will be moved apart when actuator 100 is pressed downward on body 105, in well-known fashion. A lumen 125 (FIG. 4) with an axis parallel to the axis of the holder is formed by the curved inner surfaces of jaws 115. Body 105 contains a slightly larger lumen 126 that extends upward coaxially from lumen 125. Lumen 125 normally surrounds and grips a pencil lead (not shown). The lead is dispensed from the pencil by pressing actuator 100, causing jaws 115 to open, then pulling the lead out, or letting it fall out, of the holder by a desired amount.

FIGS. 3 and 4 show side and end views, respectively, of the holder used as a capillary column holder with actuator 100 pressed downward by a user's thumb or finger (not shown), farther into body 105. This causes jaws 115 to extend outward from end 120 and springably move apart or spread to an open position, enlarging lumen 125. Jaw lumen 125 is not about the same size as internal or body lumen 126, which extends upward coaxially from lumen 125 in body 105.

A capillary column 130 (FIG. 3) with an optional pointed tip 135 is positioned along the axis of the holder and below the holder if the holder is positioned so that its tip or jaws 115 is at the bottom. If the holder is held so that jaws are at its top, column 130 would of course be positioned above the holder. If the holder is positioned horizontally, the column is positioned to the side of the tip.

When actuator 100 is pressed down, jaws 115 open and jaw lumen 125 becomes slightly larger than the outer diameter of column 130. E.g., if the outer diameter of column 130 is 360 µm (microns), lumen 125 will have an opened diameter of about 400 µm. Body lumen 126 has a fixed diameter of about 400 µm. With jaws 115 in their open position, capillary column 130 is slidably inserted manually into the pencil until only tip 135 extends below the ends of jaws 115 as shown in FIG. 5. In a factory setting, the capillary columns may be inserted into respective holders by automated machinery.

FIGS. 5 and 6 show side and end views, respectively, of the pencil with capillary column 130 in place and actuator 100 being released. Jaws 115 are moving inward in order to collapse or press against capillary column 130, clamping and holding it in place.

Pencil holders are normally supplied without a cap since the lead can be retracted and stored inside the pencil body when the pencil is not in use; thus the lead does not have a projecting end that must be protected. However if tip 135 of a capillary column is left extended outside the pencil without protection, it will likely be broken. Thus we also include a cap to protect tip 135. A cap 140 (FIG. 5) is positioned axially with the pencil in preparation to be slid over jaws 115, tip 135, and onto body 105 until the upper end of cap 140 rests against a circumferential projecting ridge, band, or stop 110. The inner diameter of cap 140 is approximately equal to the outer diameter of body 105 so that it can be slidably urged onto body 105 and remain engaged by friction fit. Thus it will not fall off but instead must be pulled off by a user. The length of cap 140 is preferably 4 cm, but other lengths can be used in order to accommodate capillaries of lengths greater than that of the pencil body. Cap 140 is preferably made of plastic, but can also be metal, wood, paper, or a combination of these materials. In one aspect, cap 140 (FIG. 5) is open at both ends. In another aspect, cap 140' (FIG. 7) is closed at its lower end. The choice of cap is a matter of user preference.

FIGS. 7 and 8 show side and end views, respectively, of the holder once again in its relaxed state with actuator 100 released and extending out maximally. Capillary column 130 securely held by jaws 115 and cap 140 is in place.

To remove column 130 from the holder, the user reverses the above procedure by removing cap 140 and pressing actuator 100 downward on body 105, thereby opening jaws 115. The user generally should carefully manually remove column 130, rather than allowing it to fall.

As indicated, mechanical pencils of the type discussed are available in a wide variety of styles and sizes. They can accommodate fragile objects having diameters of less than one mm to several mm and up to 40 cm or more in length. Thus they can be selected to accommodate capillary columns in this size range. Also holders can be especially manufactured for specific size columns. In general, columns will have diameters between 0.1 and 2 mm, so the holders should be sized accordingly, but holders can be made to accommodate columns outside this range.

A manufacturer of capillary columns would provide respective holders of the type described and package the columns in respective holders in the factory. Then the column-containing holders would be packaged in quantity in boxes, which would then be sold to end users. The end users would remove and install the individual columns when needed by removing a holder containing a column and pressing actuator 100 to dispense the column in the manner described. This will reduce breakage in transit and use and will also make it easier to dispense and install the columns.

CONCLUSION, RAMIFICATIONS, AND SCOPE

Accordingly the reader will see that, according to one or more aspects, we have provided an improved storage and carrying container for capillary columns or tubes. The container, a mechanical pencil also known as a lead holder, is simple, economical, widely available and inexpensive or easily manufactured in the proper size.

While the above description contains many specificities, these should not be construed as limitations on the scope, but as exemplifications of some presently preferred embodiments. For example, the capillary column can have a spray tip or not. Different sized capillaries can be accommodated with different sized lumens. The lumen in the jaws can be slightly less than the outer diameter of the capillary so that instead of gripping the capillary securely around its entire circumference only the edges of the lumen contact the capillary. The capillary can be coated or sheathed and the lumen sized appropriately to hold it. The gripping means of the holder can, as stated, be a friction holder, a springy tube, etc. Other types of mechanical pencils can be used in some cases, for example the type in which the lead is inserted into a top opening of the pencil and then a cap is placed in the opening and the cap is clicked repeatedly until the lead is installed.

Many other ramifications and variations are possible within the teachings. For example, all aspects of the preferred embodiment are scalable to any size. Different pencil types can be used. Other pencils hold the lead with a different jaw arrangement. All that is required is that the capillary be sized so that it can replace the lead normally held in the pencil. The outside of the pencil body can include a printable or writable surface for the specifications, i.e. size and other properties, of the individual columns contained therein.

Thus the scope should be determined by the appended claims and their legal equivalents, and not by the examples given.

The invention claimed is:

1. A method for storing, transporting, and dispensing a capillary column, comprising:
   providing an elongated mechanical holding device having a lumen diametrically sized to hold a capillary column of a predetermined size, a gripping means, and an actuator, said gripping means being operable to capture and hold said capillary column in response to operation of said actuator so as to admit said capillary column into said lumen,
   operating said actuator to open said gripping means and inserting said capillary column into said lumen, and operating said actuator to close said gripping means in order to securely hold said capillary column.

2. The method of claim 1, further including positioning a cap over an end of said holding device so as to protect any part of said capillary column that projects out of said holding device.

3. The method of claim 2 wherein said cap is made from a material selected from the group consisting of plastic, metal, wood, and paper.

4. The method of claim 1 wherein said body of said holding device is of sufficient length to fully enclose said capillary column.

5. The method of claim 1 wherein said gripping means comprises a plurality of jaws that can be opened and closed by operating said actuator.

6. The method of claim 1 wherein said holder is a mechanical pencil.

7. A method for storing, transporting, and dispensing capillary columns, comprising:
   providing a mechanical holder having an interior lumen and a plurality of jaws, said jaws also including a jaw lumen coaxial with said interior lumen, said jaws being normally closed when at rest,
   providing an actuator, said actuator arranged to open said jaws when pressed and to allow said jaws to close when released,
   providing a capillary column, said column having diameter equal to or larger than said lumen of said jaws and sized to fit within said interior lumen so that said column can be slidably inserted into said holder when said jaws are open,
   pressing said actuator to open said jaws,
   slidably inserting said capillary column into the body of said holder,
   releasing said actuator to permit said jaws to springably close,
   whereby said capillary column is securely held within said holder by said jaws.

8. The method of claim 7, further including providing a cap that is slidably engagable with said body of said holder, and sliding said cap onto said body of said holder,
   whereby when said capillary column extends outside said jaws, said cap protects said capillary column.

9. The method of claim 8 wherein said cap is made from materials selected from the group consisting of plastic, metal, wood, and paper.

10. The method of claim 7 wherein said body of said holder is of sufficient length to fully enclose said capillary column.

11. The method of claim 7 wherein said plurality of jaws comprise a plurality of sector-shaped members that define a central lumen and that can be opened and closed by said actuator.

12. The method of claim 7 wherein said holder is a mechanical pencil.

13. The method of claim 7 wherein said body of said holder is of sufficient length to fully enclose said capillary column.

14. A method for storing, transporting, and dispensing capillary columns, comprising:
   providing a mechanical holder having an interior lumen and a gripping means, said gripping means including a gripping lumen coaxial with said interior lumen, said gripping means being normally closed when at rest, providing an actuator, said actuator arranged to open said gripping means when pressed and to allow said gripping means to close when released, providing a capillary column, said column having diameter equal to or larger than said lumen of said gripping means and smaller than said interior lumen so that said column can be slidably inserted into said holder when said jaws are open, pressing said actuator to open said gripping means, slidably inserting said capillary column into the body of said holder, releasing said actuator to permit said gripping means to springably close, whereby said capillary column is securely held within said holder by said gripping means.

15. The method of claim 14, further including providing a cap that is slidably engagable with said body of said holder, and sliding said cap onto said body of said holder, whereby when said capillary column extends outside said jaws, said cap protects said capillary column.

16. The method of claim 15 wherein said cap is made from materials selected from the group consisting of plastic, metal, wood, and paper.

17. The method of claim 14 wherein said gripping means comprises a plurality of sector-shaped jaws that define a central lumen and that can be opened and closed by said actuator.

18. The method of claim 14 wherein said holder is a mechanical pencil.

19. The method of claim 14 wherein said mechanical holder is arranged to hold and dispense capillary columns having a diameter between 0.1 millimeter and 2 millimeters.

20. The method of claim 14 wherein said holder is a mechanical pencil and said gripping means comprises a plurality of sector-shaped jaws that define a central lumen and that can be opened and closed by said actuator.

* * * * *